(12) United States Patent
Demian

(10) Patent No.: US 6,889,088 B2
(45) Date of Patent: May 3, 2005

(54) BUNION TREATING DEVICE

(76) Inventor: Bassem M. Demian, 430 Shore Line Pl., Brick, NJ (US) 08723

( * ) Notice: Subject to any disclaimer, the term of this patent is extended or adjusted under 35 U.S.C. 154(b) by 466 days.

(21) Appl. No.: 09/880,633

(22) Filed: Jun. 13, 2001

(65) Prior Publication Data

US 2002/0062140 A1 May 23, 2002

Related U.S. Application Data

(63) Continuation-in-part of application No. 09/716,567, filed on Nov. 20, 2000, now Pat. No. 6,862,481.

(51) Int. Cl.⁷ .................................................. A61N 1/08
(52) U.S. Cl. .......................... 607/72; 607/50; 607/144; 607/149; 128/898
(58) Field of Search .............................. 607/72, 46, 88, 607/50, 48, 49, 2, 144, 149, 76, 68, 148, 70; 128/898

(56) References Cited

U.S. PATENT DOCUMENTS

| | | | |
|---|---|---|---|
| 2,827,049 A | | 3/1958 | Scholl .......................... 128/153 |
| 3,650,276 A | * | 3/1972 | Burghele et al. .............. 607/72 |
| 4,026,301 A | * | 5/1977 | Friedman et al. .............. 607/72 |
| 4,325,367 A | * | 4/1982 | Tapper ......................... 607/144 |
| 4,326,534 A | * | 4/1982 | Axelgaard et al. ............. 607/43 |
| 4,632,103 A | | 12/1986 | Fabricant et al. ........... 128/157 |
| 4,729,369 A | | 3/1988 | Cook ........................... 128/81 |
| 4,930,504 A | * | 6/1990 | Diamantopoulos et al. ... 607/88 |
| 4,940,046 A | | 7/1990 | Jacoby ......................... 128/81 |
| 5,094,226 A | | 3/1992 | Medcalf et al. ............... 128/25 |
| 5,281,219 A | * | 1/1994 | Kallok ......................... 607/72 |
| 5,578,065 A | * | 11/1996 | Hattori et al. ................ 607/46 |
| 5,674,267 A | * | 10/1997 | Mir et al. ..................... 607/72 |
| 5,922,012 A | * | 7/1999 | Sakano ......................... 607/46 |
| 6,341,237 B1 | * | 1/2002 | Hurtado ...................... 607/148 |
| 6,456,884 B1 | * | 9/2002 | Kenney ........................ 607/48 |

OTHER PUBLICATIONS

Muscle Re–Education Treatment Options, J. Stephen Guffey, 1996.

* cited by examiner

Primary Examiner—Fadi H. Dahbour
(74) Attorney, Agent, or Firm—Carella Byrne Bain et al.; John G. Gilfillan, III; William Squire

(57) ABSTRACT

A pulse generating apparatus has two like output channels that apply generated pulse signals of selected characteristics to two electrodes attached to a strap, each electrode receiving a different signal. The strap is attached to the foot so that the electrodes are positioned to stimulate with an electrical signal the abductor hallucis muscle of the foot to correct an imbalance due to overpowering by the adductor hallucis muscle in the large toe. The signal strengthens the abductor hallucis muscle so that eventually it regains strength sufficient to counter balance the imbalance effect of the stronger adductor hallucis muscle and alleviate the bunion condition in the large toe. The electrical signal generator generates signals that are pulses that are adjustable in frequency, modulation, pulse width and amplitude with modified square waves. In a second embodiment, the abductor digiti minimi brevis muscle is overpowered by the flexor digitorum (3ʳᵈ plantar interosseus), in respect of the small toe causing Tailors Bunion. In this case, the two electrodes are attached via a strap to the foot so that the electrodes are positioned to stimulate with an electrical signal the abductor digiti minimi brevis muscle to strengthen this muscle and correct the bunion condition for the small toe.

21 Claims, 7 Drawing Sheets

LOAD MODE: 1M OHM
(OPEN CIRCUIT)
Ver. MODE: CH1
VOLT/DIV: 50.0V
TIME/DIV: 0.1MS

LOAD MODE: 500.00 OHM
VER. MODE: CH1
TIME/DIV: 0.1MS
VOLT/DIV: 5.0V

BUNION TREATING DEVICE

This application is a continuation in part of application Ser. No. 09/716,567 filed Nov. 20, 2000, now U.S. Pat. No. 6,862,481, and incorporated by reference in its entirety herein.

FIELD OF THE INVENTION

This invention relates to podiatric devices, and more particularly, to devices for the correction of bunion conditions in the foot.

BACKGROUND OF THE INVENTION

U.S. Pat. No. 5,665,060 discloses a bunion treatment apparatus and method for minimizing the forces applied to a bunion and includes a planar main portion and a planar built-up portion constructed of flexible padding material. Strain relief cutouts are provided as well as a toe loop to prevent tearing of the main portion. This apparatus is provided merely to alleviate the discomfort of the condition rather than eliminating the condition.

U.S. Pat. No. 2,827,049 provides a bunion pad and suffers from a similar deficiency.

U.S. Pat. No. 4,729,369 discloses a toe splint and bunion correction device which attempts to correct the condition with a splint device which straightens the toe including a splint member and a Velcro fastener for securing the splint member to the foot. The splint member is plastic and is molded to accommodate the foot.

In U.S. Pat. No. 4,940,046 a pliable protector cushion pad device is disclosed for the big toe or hallux.

U.S. Pat. No. 4,632,103 shows a bandage to reduce bunion pain.

All of the above patents either try to minimize the pain of the bunion or use mechanical devices to correct the condition.

*Isoelectronic Rehabilitation Program—Advanced Clinical Applications—Podiatric Electrotherapy Applications* by Joe Kleinkort, 1989, 1992, is a manual that suggests electrotherapy applications for relaxation of muscle spasm, prevention or retardation of disuse atrophy, increasing local blood circulation, muscle reeducation, immediate postsurgical stimulation of calf muscles to prevent venous thrombosis and maintaining or increasing the range of motion. This manual discloses placement of electrodes to alleviate pain in various conditions in the ankle, feet and knee, and stimulation of muscles in cases of immobilization, An article entitled *Investigations on the origin of Hallux Valgus by Electromygraphic Analysis* by Takebe K. Shimazaki __1 Kobe J Medical Science 1981 August: 27(4) :139–58 discloses electromyographic analysis on the physiopathology of the Hallus Valgus and toes/physiopathology.

Stephen Guffey discloses, in a publication dated 1996, muscle reeducation employing electrical stimulation including frequencies, pulse duration, polarity, duty cycle, ramp, intensity, treatment time, how often, and electrode placement.

Electrode stimulation and muscle reeducation have generally been related to pain reduction. None of the above articles, however, relate to the problem of bunions and how to treat and correct the condition.

SUMMARY OF THE INVENTION

The present inventor recognizes that mechanical correction of the bunion condition is not satisfactory and a need is recognized for a more sophisticated device to correct the bunion condition. The pain reduction and muscle reeducation articles using electrotherapy have dealt primarily with leg and back problems or foot/ankle problems not associated with bunions. Present solutions for bunions is typically related to mechanical devices as disclosed in the aforementioned patents which approach correcting the problem with brute force mechanical splints and padding.

In contrast to the mechanical devices of the prior art for correction of Tailors Bunion conditions in the foot, a method of correcting a Tailors Bunion condition in a foot according to the present invention comprises the step of applying an electrical signal to the abductor digiti minimi brevis muscle to strengthen this muscle to counter balance the strength of the flexor digitorum longus muscle and therefore correct Tailors Bunion condition.

In one aspect, the method includes means for applying repetitive cycles of electrical pulses to the abductor digiti minimi brevis muscle.

In a further aspect, the pulses are modified square waves at a pulse repetition rate of 2 Hz to 150 Hz, a pulse width of about 60:s to 250:s.

The method in a further aspect includes cyclically increasing the pulse width.

In a further aspect, the method includes wrapping the foot with a strap, attaching at least one electrode to the strap with the electrode abutting the foot and then applying the electrical signal to the electrode.

The method in a further aspect further includes optimizing the signal to maximize the rection by adjusting the signal parameters until an optimum signal is generated.

A bunion correction device according to the present invention comprises means for attaching at least one electrode to the foot for applying an electrical signal to the abductor digiti minimi brevis muscle in the foot for strengthening this muscle to counter balance the strength of the foot flexor digitorum muscle and signal generator means for generating the electrical signal and applying the generated signal to the means for attaching.

In one aspect, the means for attaching comprises strap means for encircling the foot and means for securing the at least one electrode to the strap means for abutting the foot when the strap means is attached to the foot.

In a further aspect, the generating means includes means for applying a generated signal to two electrodes.

In a further aspect, the signal generator includes means for generating a plurality of pulses and includes means for setting the pulses in the range of 0–80 mA peak with either a positive or negative pulse into a 500 ohm load.

In a further aspect, the means for generating includes means for generating the pulse at a frequency in the range of about 2 Hz to 150 Hz.

In a further aspect, the means for generating includes means for generating the pulse with a width in the range of about 60:s to 250:s.

In a still further aspect, the means for generating includes means for generating bursts of said pulses of about 7 pulses at a maximum pulse rate.

In a further aspect, the means for generating includes means for generating bursts of pulses twice a second.

In a further aspect, the strap means comprises a strap for encircling the foot.

In a still further aspect, two spaced electrodes are arranged on the strap means for overlying the abductor digiti minimi brevis muscle of the foot in two spaced locations.

In a further aspect, the means for generating includes means for independently generating the two signals and applying a different signal to each electrode.

IN THE DRAWING

Figure 4:
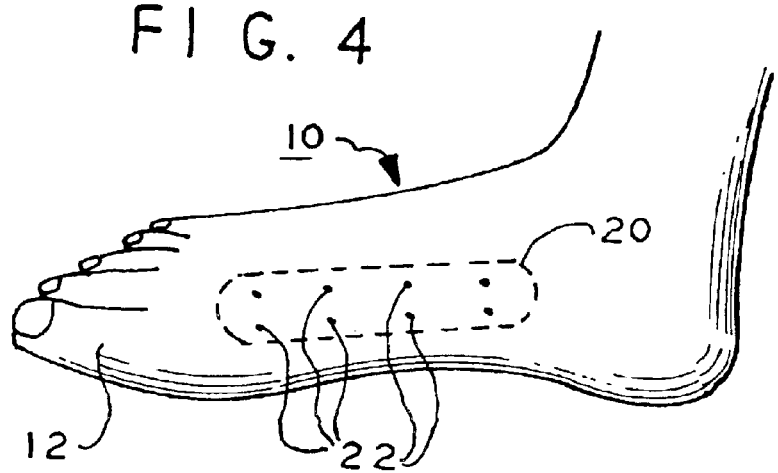
FIGS. 4 and 5 are respective similar side views of a foot which show generally the placement of electrodes for the correction of the bunion condition and a device according to an embodiment of the present invention employing electrodes for the correction of the bunion condition with electrical signals.
Figure 15:
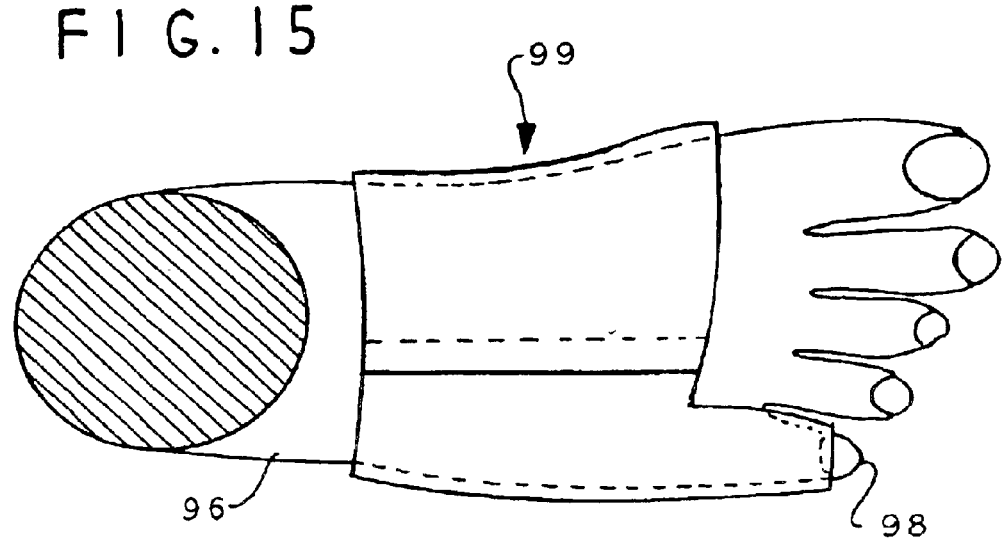
FIG. 15 is a is a plan view of the foot and device of FIG. 17 in place.
Figure 16:
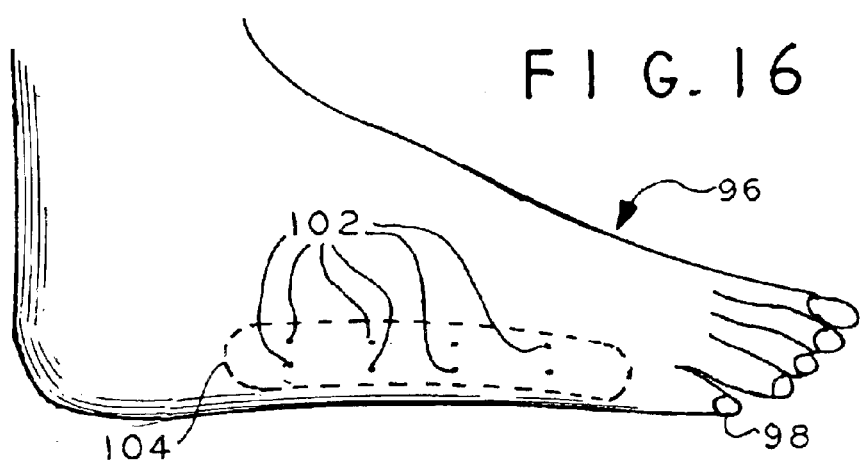
Figure 17:
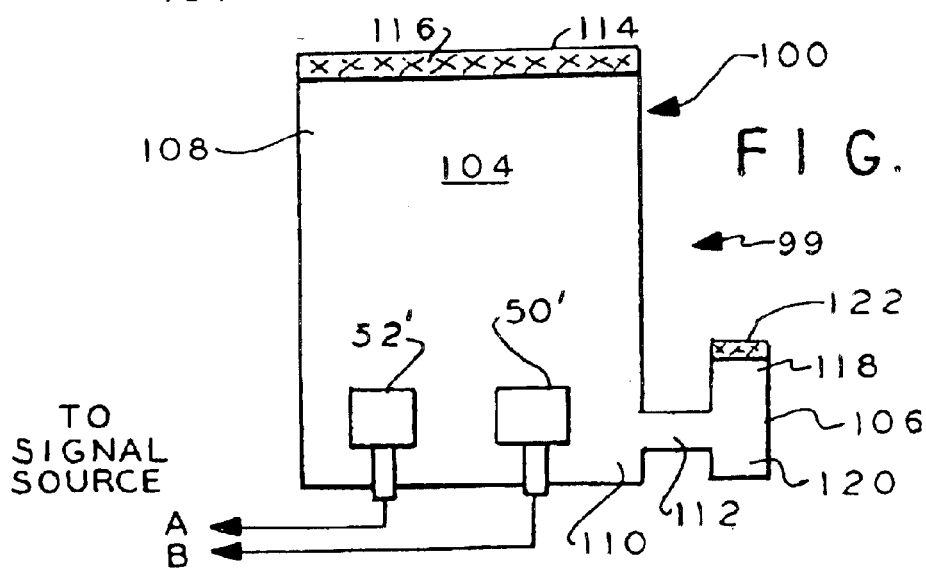

FIG. 16 is a side view of a foot similar to FIG. 4 showing generally the placement of electrodes for the correction of the Tailors Bunion condition in the small toe according to an embodiment of the present invention employing electrodes for the correction of the Tailors Bunion condition with electrical signals; and FIG. 17 is a plan view of the device of FIG. 15 prior to attachment to a foot with representative electrodes attached for electrically correcting the Tailors Bunion condition

DETAILED DESCRIPTION OF THE DRAWINGS

Figure 1:
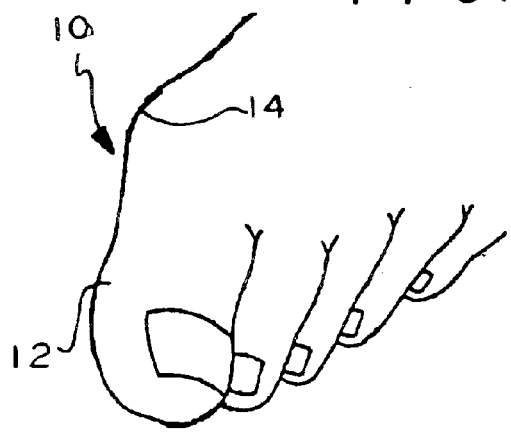
FIG. 1 is a perspective view of a foot exhibiting a bunion condition.
Figure 2:
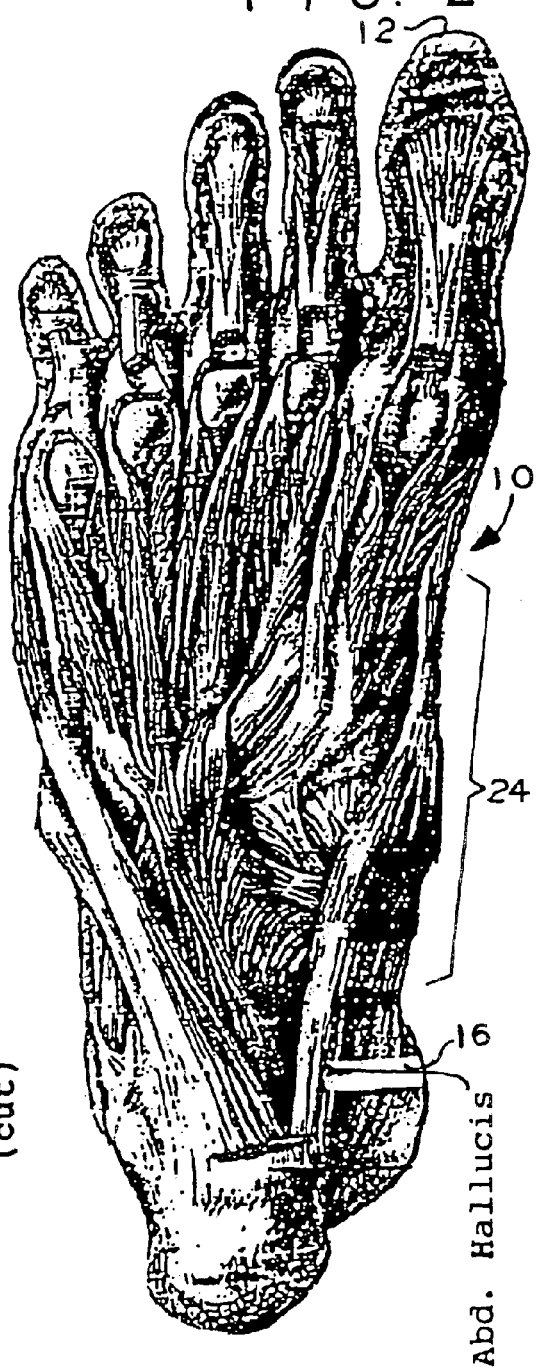
FIG. 2 is a top plan view of the anatomy of a foot showing the abductor hallucis muscle in the foot.
Figure 3:
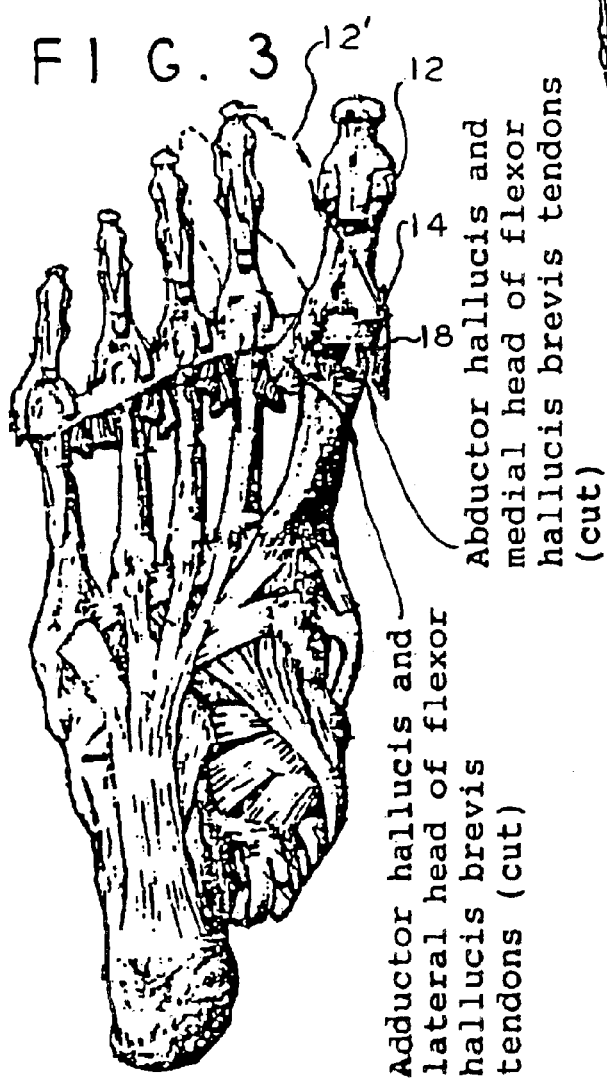
FIG. 3 is a top plan view of the anatomy of a foot showing the abductor hallucis and adductor muscles (cut away) in the foot which control the large toe.

In FIG. 1, foot 10 big toe 12 has a bunion 14. In FIG. 2, one muscle of the foot for controlling the big toe is the abductor hallucis muscle 16. In FIG. 3, a second muscle of the big toe is the adductor hallucis muscle 18 (shown cut away but in practice has an extent corresponding generally to the extent of the abductor hallucis muscle in FIG. 2. The present invention is a result of the recognition that the bunion 14 (shown in phantom in FIG. 3) is caused by the adductor hallucis muscle becoming stronger than the abductor hallucis muscle. Normally, in a healthy foot both muscles are of equal strength and counter balance the forces of each other in the normal quiescent state of the big toe.

However, over time due to mis-fitting shoes or due to genetic or disease problems, the strengths of the two muscles become different. The adductor muscle eventually overpowers the abductor muscle and pulls the big toe over to one side toward the other toes as shown in phantom in FIG. 3 by toe 12'. The abductor muscle extends for the length of the foot as shown in FIG. 1 and is adjacent to both the side and top side surfaces of the foot.

It is known generally that muscles can be stimulated by electrical signals and this knowledge has been used to relieve pain due to muscle conditions, typically in the back, foot/ankle or leg. See the articles in the introductory portion. However, the present invention is a recognition that the bunion is due to a imbalance in the abductor and adductor hallucis muscles and that the abductor muscle can be strengthened by the application of electrical pulses thereto. The prior art has typically approached the correction of bunions with brute force by the use of mechanical devices and splints. The use of electrical signals to strengthen the abductor hallucis muscle of the present invention corrects the problem by reducing the one sided impact imbalance of the stronger adductor hallucis muscle in persons exhibiting bunions.

In FIG. 4, foot 10 is shown with a region 20 in which the abductor hallucis muscle is located. One or more electrodes are placed in this region and an electrical signal is applied to the electrodes to stimulate and repetitively relax and tighten the abductor hallucis muscle. The exact location can be determined empirically for each patient in order to ascertain the most optimum portion of the abductor hallucis muscle that is responsive to the electrical signal(s) for strengthening the muscle. This might take some trial and error until the optimum repositioning of the big toe 12 is observed. It is recommended that the major site of the abductor hallucis muscle be identified and the electrodes applied to this site. This site is believed to occur in the region 24, FIG. 2, in regard to the abductor hallucis muscle, which might vary of course from individual to individual.

Figure 5:
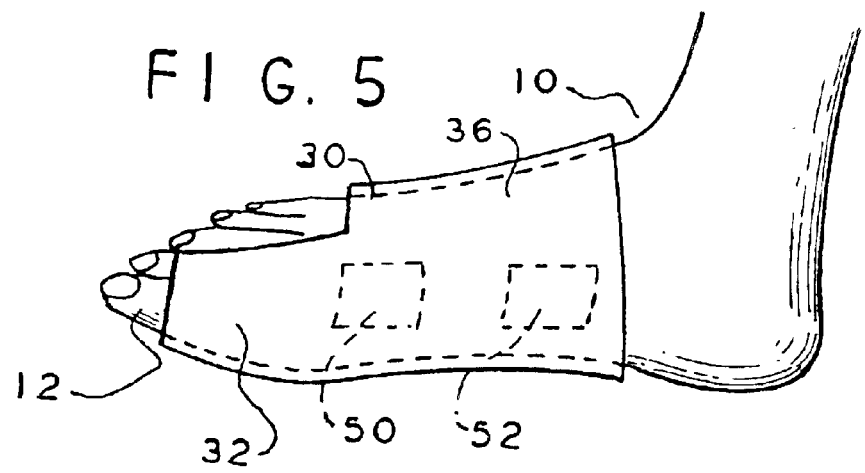
Figure 6:
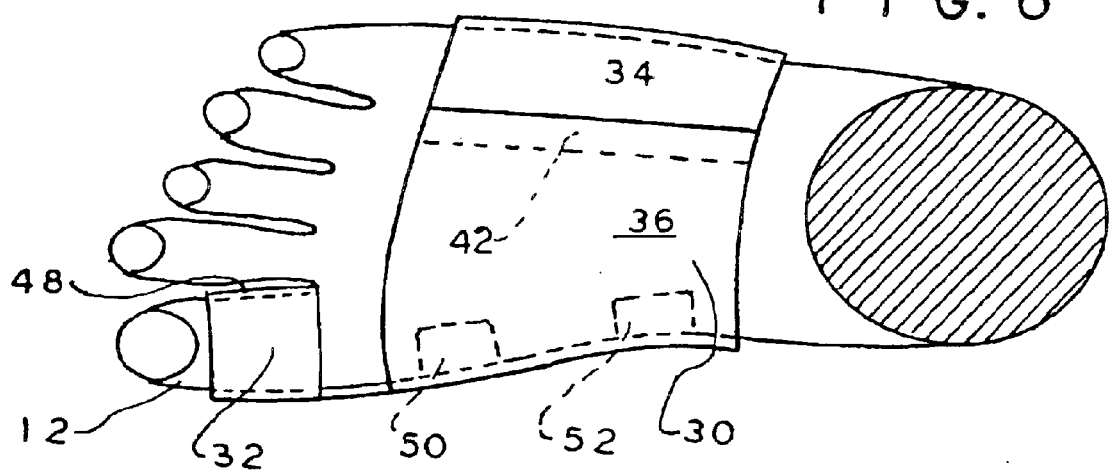
FIG. 6 is a plan view of the foot and device of FIG. 5.
Figure 7:
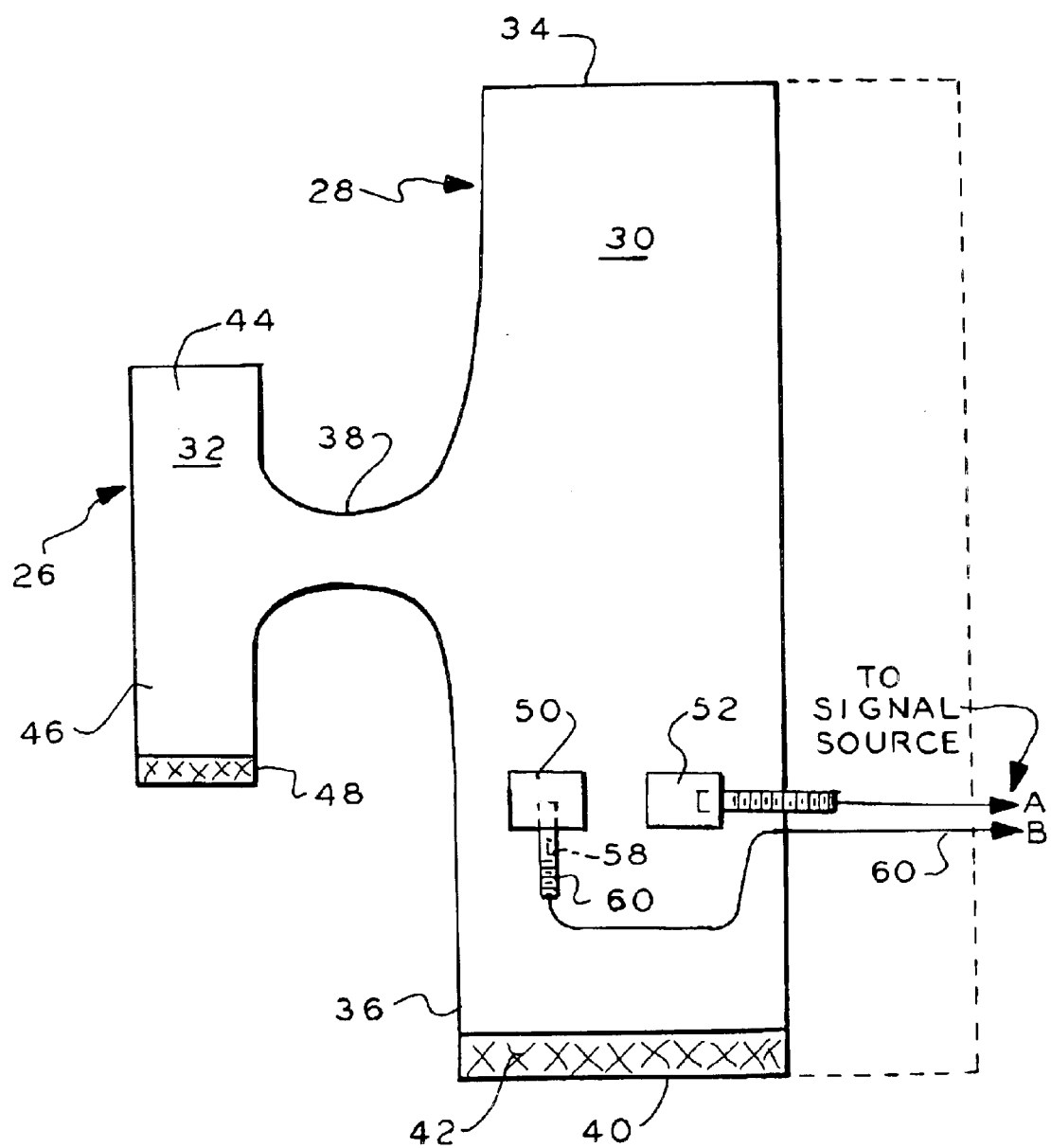
FIG. 7 is a plan view of the device of FIGS. 5 and 6 prior to attachment to a foot with representative electrodes attached for electrically correcting the bunion condition.

In FIG. 7, device 26 comprises a strap 28 formed of felt, foam or similar soft cushioning materials the composition of which is not important to the present invention other than it be electrical insulating material. Strap 28 preferably comprises two substraps 30 and 32. Substrap 30 comprises a generally rectangular member with two opposing legs 34 and 36 of about the same width and attached one piece and integral with connecting member 38. Legs 34 and 36 are of like width from left to right in the figure. The end 40 of leg 36 has a strip 42 of Velcro hook members, a trademark for a hook and loop fastener well known and commercially available. The leg 34 and leg 36 overlap when wrapped about the foot as shown in FIGS. 5 and 6. The leg 36 strip 42 hooks engage the leg 34 which comprises loop type of fabric, or in the alternative, may include a strip (not shown) of Velcro loop material mating with the hook material strip 42. The hook and loop material releasably attach the overlapping two legs 34 and 36 of the substrap 30 as shown.

Figure 12A:
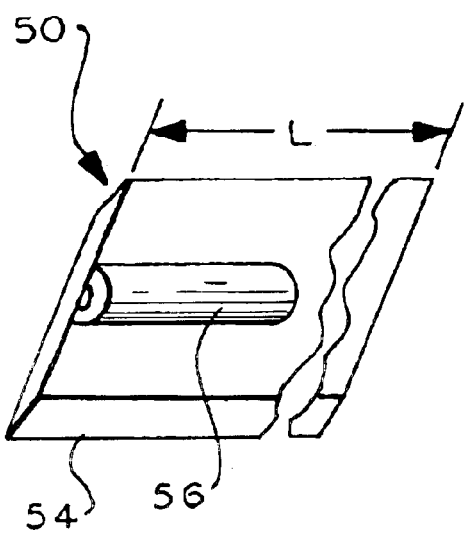
FIG. 12a is an isometric view of the electrode of FIG. 12 without the electrical terminal in place.
Figure 12:
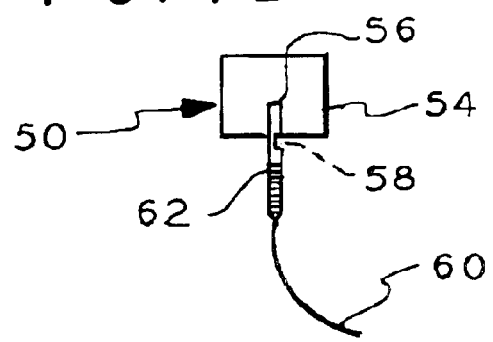
FIG. 12 is a top plan view of a representative electrode for applying a bunion correction signal to the foot.

Substrap 32 comprises two legs 44 and 46 and Velcro hook strip 48. Legs 44 and 46 attach similarly as legs 34 and 36 about the big toe 12. Substrap 32 is connected to substrap 30, and integral one piece therewith by the connecting member 38. In FIG. 7, two electrodes 50 and 52 in this embodiment are attached to substrap 30 The electrodes 50 and 52 are identical and a description of electrode 50 is representative. In FIGS. 12 and 12a, electrode 50 comprises a electrically conductive pad 54 which may be conductive elastomeric or plastic material. The pad 54 has a hollow somewhat tubular terminal connector 56 molded integral therewith. The pad 54 is square but may be other shapes. This electrode 50 is commercially available from the Lumiscope Company of Edison, N.J. as a kit with other components of the electrical signal generator to be described below as model SW1000 Transcutaneous Electrical Nerve Stimulator.

An electrical terminal 58 which is an elongated metal wire as typical in electrical connections and terminals, fits inside of the connector 56 to apply an electrical pulse signal to the pad 54. The pad 54 on a side opposite the connector 54 may receive an electrically conductive gel as known in this art for providing good electrical coupling to a local applied portion of the skin of the foot 10. An electrically conductive conductor 60 is connected to terminal 58 at one conductor end and to plug connector 62, FIG. 11, at the other conductor end.

Figure 8:
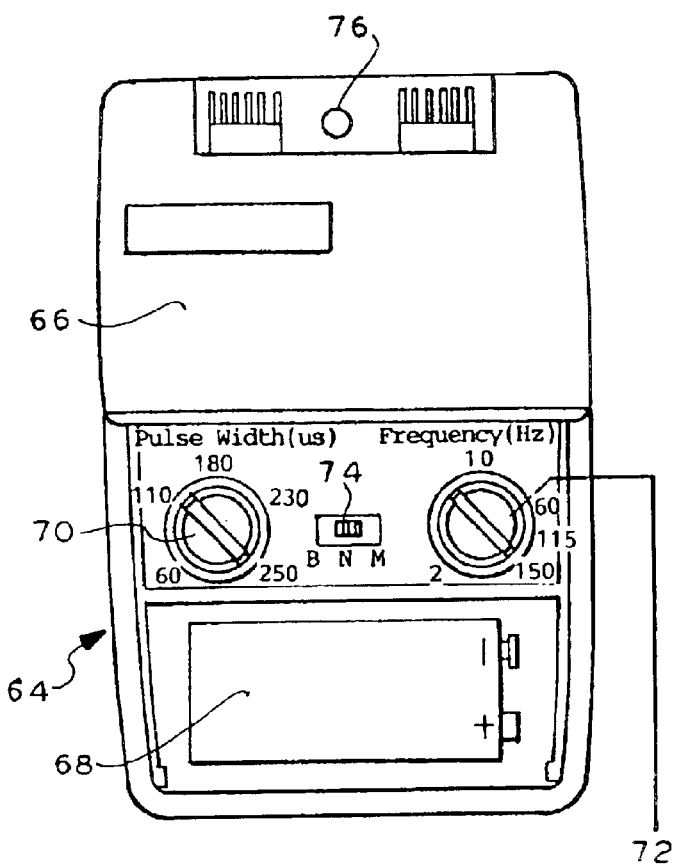
FIG. 8 is a front elevation view of an electrical signal generator for use with the device of FIGS. 5, 6 and 7.
Figure 9:
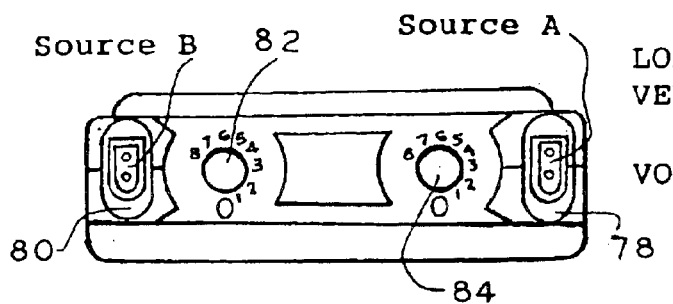
FIG. 9 is a top plan view of the generator of FIG. 8.

In FIG. 8, electrical signal generator apparatus 64 has a housing 66 which receives a battery 68 (a conventional 9 volt transistor battery) with its electrical connection to the apparatus 64 and the housing cover not shown. The apparatus has a circuit which is commercially available (not shown and within the housing) and is available from the Lumiscope Company. Two control knobs 70 and 72 control the respective pulse width and frequency of the alternating current signal produced by the apparatus 64. A mode selector switch 74 selects burst (B), normal (N) and modulation (M) modes of the generated pulses. A power indicator light 76 is included. In FIG. 9, channel output receptacles 78 and 80 provide two parallel identical output signals generated by the apparatus 64. Knob 82 controls channel on/off state for receptacle 80 and the output signal amplitude for this receptacle. Knob 84 controls channel on/off state for receptacle 78 and the output signal amplitude for this receptacle.

Figure 10A:
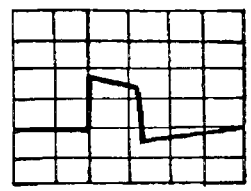
FIGS. 10a and 10b are waveform graphs of representative signals produced by the generator of FIG. 8.
Figure 10B:
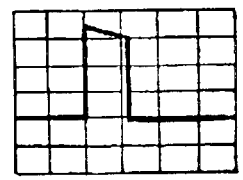

The circuit of apparatus 64 provides dual identical channels which are electrically isolated. The circuit is a pulse generator for generating approximate adjustable square waves as shown in FIGS. 10a and 10b which are self explanatory. The amplitude of each channel is independently controlled, but otherwise the parameters of the signals of the two channels is the same as controlled by knobs 70 and 72 and mode select switch 74. The pulse amplitude is adjustable by knobs 82 and 84 in a range of 0–80 mA peak either with a positive pulse or negative pulse into a 500 ohm load for each channel. The pulse frequency is adjustable in the range of 2 Hz to 150 Hz. The pulse width is adjustable in the range of about 60:$\mu$s to 250: $\mu$s.

The apparatus has a modulation mode. The modulation mode is one where the pulse width is automatically varied in a cyclic pattern over an interval of nominally 4.0 seconds. The pulse width decreases linearly over a period of 1.0 seconds from the control setting value to a value which is decreased 40% maximum. The narrow pulse width will continue for 1.5 seconds maximum, then increase linearly over a 1.5 second period to its original value. The cycle is then repeated.

The apparatus also has a burst mode in which bursts of seven pulses are provided at a maximum pulse rate. The bursts occur twice a second.

The wave form as shown in FIGS. 10a and 10b are modified square waves with zero net direct current (DC) component. All of the adjustable parameters are set at the midpoint of the specified range. The apparatus has a voltage of 0–110 volts maximum either positive or negative pulse (open circuit). There is a maximum charge per pulse of 16 micro coulombs. The values may vary in a range of +/−20%. This apparatus is normally commercially available for treatment only of pain, chronic or adjunct to management of post surgical and post traumatic acute pain problems. However, as disclosed herein it may also be used to correct bunion conditions. The apparatus is available with the restriction that transcutaneous electrical nerve stimulation is of no known curative value other than pain relief.

Figure 11:
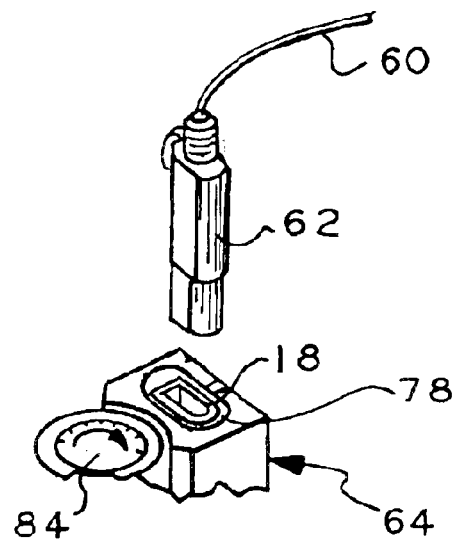
FIG. 11 is an isometric view of a portion of the top of the generator of FIG. 9 showing the attachment of a the signal output cable of the generator to a representative output connector, there being two output connectors in the generator.

The connector 62 is mated in receptacle 78, FIG. 11 to connect the electrode 50 to the output signal. The electrodes 50 and 52, FIG. 7, are bonded by a Velcro fastener to the strap 28, FIG. 7, leg 36. The location of the electrodes is determined for a given patient and determined on a case by case basis. The signal parameters are varied until optimum correction of the bunion is noted. This requires setting of the pulse parameters by the user during the initial set up. The user will note various nerve reactions to the electrical signals and by observation can determine optimum electrical impulses. The various parameters of the pulses are set to optimize the visual and physical results. While the particular electrical signal parameters are given herein, they are given by way of example, and not limitation. Other electrical signals of pulses of different shapes, currents, amplitudes and wave forms may also be used according to a given condition being corrected. Also, the shape and material of the strap is by way of example and not limitation.

Other devices for applying the electrical signals may be utilized, the device described herein being given by example only. The important aspect is that the abductor muscle is strengthened sufficiently so that the forces on the big toe muscles balance. The big toe thus returns to its normal position in response to the treatment described herein.

Figure 13:
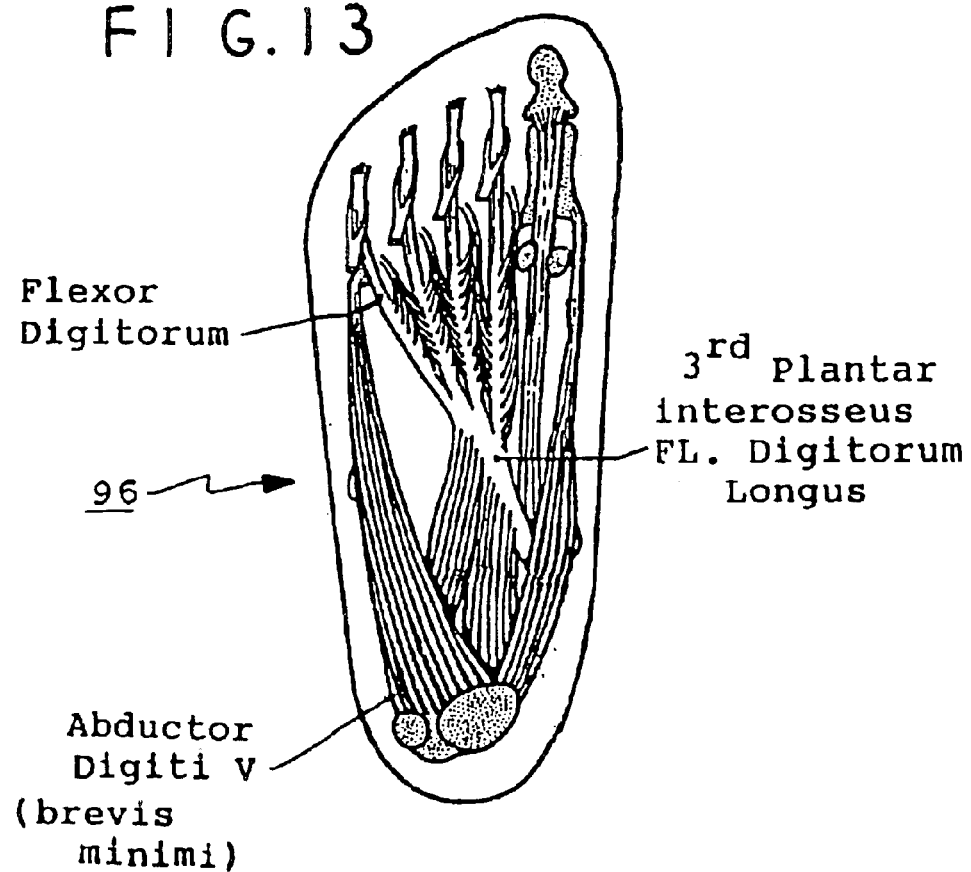
FIG. 13 is a top plan view of the anatomy of a foot showing the abductor digiti V and flexor digitorum muscles in the foot.
Figure 14:
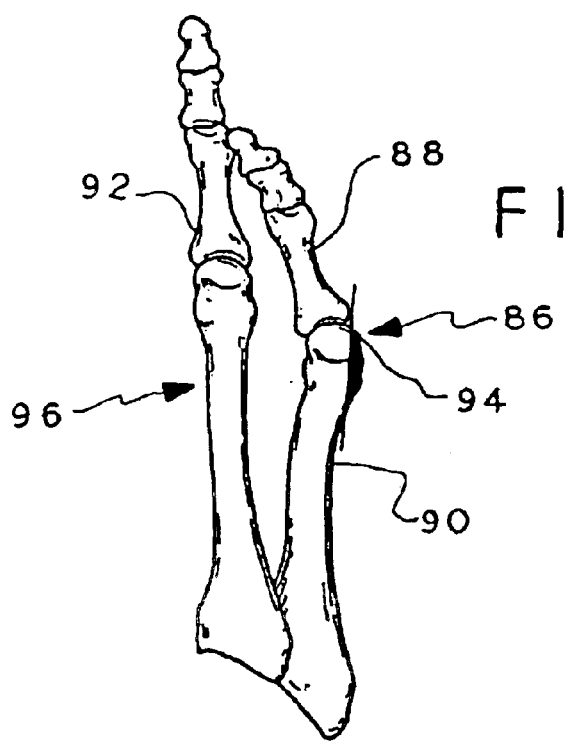
FIG. 14 is a view of the distorted bones of the small toe due to Tailors Bunion condition.

In FIG. 14, a second bunion condition is shown in the foot. This condition is known as Tailors Bunion. The small toe 86 bone 88 (the fifth toe) is pulled inward toward toe 92 (the fourth toe) relative to bone 90. The bone 88 is bent at joint 94. In FIG. 13, this bunion condition in caused in foot 96 by the stronger muscle flexor digitorum longus overpowering the weaker muscle abductor digiti v. or otherwise known as the abductor digiti minimi brevis.

In FIG. 15, the foot 96 small toe 98 is shown electrically adjusted by impulses produced by device 99. In FIG. 17, device 99 comprises a strap 100 to which two electrodes 50' and 52' (which may be identical to electrodes 50 and 52) are attached in a manner similar to the attachment of electrodes 50 and 52, FIG. 7. Electrodes 50' and 52' are also operated similarly as electrodes 50 and 52 by pulse generator 64, FIG. 8, described above, except in this case the pulse parameters and electrode positions are adjusted accordingly to correct for the Tailors Bunion condition. This adjustment and the level of currents and pulse parameters are also determined empirically for each implementation.

In FIG. 16, foot 96 is shown with a region 104 in which the abductor digiti minimi brevis muscle is located. One or more electrodes 102 corresponding to electrodes 50' and 52' are placed in this region and an electrical signal is applied to the electrodes to stimulate and repetitively relax and tighten the abductor digiti minimi brevis muscle. The exact location can be determined empirically for each patient in order to ascertain the most optimum portion of the abductor digiti minimi brevis muscle that is responsive to the electrical signal(s) for strengthening the muscle. This might take some trial and error until the optimum repositioning of the small toe 98 is observed. It is recommended that the major site of the abductor digiti minimi brevis muscle be identified and the electrodes applied to this site. This site is believed to occur in the region 104, FIG. 16, in regard to the abductor digiti minimi brevis muscle, which might vary of course from individual to individual.

In FIG. 15, the foot 96 small toe 98 is shown electrically adjusted by impulses produced by device 99. In FIG. 17, device 99 comprises a strap 100 to which two electrodes 50' and 52' (which may be identical to electrodes 50 and 52) are attached in a manner similar to the attachment of electrodes 50 and 52, FIG. 7. Electrodes 50' and 52' are also operated similarly as electrodes 50 and 52 except in this case the pulse parameters and electrode positions are adjusted accordingly to correct for the Tailors Bunion condition. This adjustment and the level of currents and pulse parameters are also determined empirically for each implementation.

In FIG. 17, device 98 strap 100 is also formed of felt, foam or similar soft cushioning materials the composition of which is not important to the present invention other than it be electrical insulating material similarly as strap 28 described above. Strap 100 preferably comprises two substraps 104 and 106. Substrap 104 comprises a generally rectangular member with two opposing legs 108 and 110 of about the same width and attached one piece and integral with connecting member 112. Legs 108 and 110 are of like width from left to right in the figure. The end 114 of leg 108 has a strip 116 of Velcro hook members. The legs 108 and 110 overlap when wrapped about the foot as shown in FIG. 15. The strip 116 hooks engage the leg 110 which comprises loop type of fabric, or in the alterative, may include a strip (not shown) of Velcro loop material mating with the hook material strip 116.

Substrap 32 comprises two legs 118 and 1120 and Velcro hook strip 122. Legs 118 and 120 attach about the small toe 98. Substraps 118 and 120 are integral one piece and attached to connecting member 112. Two electrodes 50' and 52' in this embodiment are attached to substrap 108. The electrodes 50' and 52' may be identical and are as described above in connection with electrodes 50 and 52.

While a strap is shown about the big and small toes these are optional and are provided in case a need arises for electrodes to be attached thereto.

It will occur to one of ordinary skill that modifications may be made to the disclosed embodiments without departing from the scope of the invention as defined in the appended claims. The disclosed embodiments are given by way of illustration and not limitation. For example, while the foot muscles for the big toe involving a bunion condition are corrected herein, other muscles involving other limb distortions due to muscle imbalance may also be corrected by applying electrical signals to strengthen certain of such other muscles.

What is claimed is:

1. A bunion correction device comprising:
   means for attaching at least one electrode to the foot for applying an electrical signal to the abductor digiti minimi brevis muscle in the foot for strengthening the abductor digiti minimi brevis muscle to counter balance the strength of the foot flexor digitorum muscle to correct a bunion in the small toe; and
   signal generator means for generating the electrical signal and applying the generated signal to the at least one electrode.

2. The device of claim 1 wherein the means for attaching comprises strap means for encircling the foot and means for securing the at least one electrode to the strap means for abutting the foot when the strap means is attached to the foot.

3. The device of claim 1 wherein the generating means includes means for applying a generated signal to two electrodes.

4. The device of claim 1 wherein the signal generator includes means for generating a plurality of pulses and includes means for setting the pulses in the range of 0–80 mA peak with either a positive or negative pulse into a 500 ohm load.

5. The device of claim 4 wherein the means for generating includes means for generating the pulse at a frequency in the range of about 2 Hz to 150 Hz.

6. The device of claim 4 wherein the means for generating includes means for generating the pulse with a width in the range of about 60:s to 250:s.

7. The device of claim 4 wherein the means for generating includes means for generating bursts of said pulses of about 7 pulses at a maximum pulse rate.

8. The device of claim 4 wherein the means for generating includes means for generating bursts of pulses twice a second.

9. The device of claim 2 wherein the strap means comprises a strap for encircling the foot.

10. The device of claim 2 including two spaced electrodes arranged on the strap means for overlying the abductor digiti minimi brevis muscle of the foot in two spaced locations.

11. The device of claim 3 wherein the means for generating includes means for independently generating the two signals and applying a different signal to each electrode.

12. A method of correcting a bunion condition in a foot comprising the step of applying an electrical signal to the abductor digiti minimi brevis muscle to strengthen the abductor digiti minimi brevis muscle and counter balance the strength of the flexor digitorum muscle to correct for an imbalance between the two muscles.

13. The method of claim 12 including the step of applying repetitive cycles of electrical pulses to the abductor muscle.

14. The method of claim 13 including the step of generating pulses that are modified square waves at a pulse repetition rate of 2 Hz to 150 Hz and at a pulse width of about 60:s to 250:s.

15. The method of claim 14 including the step of cyclically increasing the pulse width.

16. The method of claim 15 including the step of varying the pulse width in repetitive four second cycles.

17. The method of claim 12 including the step of wrapping the foot with a corresponding strap, attaching at least one electrode to the strap with the electrode abutting the foot and then applying the electrical signal to the electrode.

18. The method of claim 12 including optimizing the signal to maximize said correction by adjusting the signal parameters until an optimum signal is generated.

19. The method of claim 12 including periodically applying the signal to the foot.

20. The method of claim 19 including applying the signal in the range of 15–30 minutes daily.

21. The method of claim 12 including cyclically tightening and relaxing the abductor digiti minimi brevis muscle with the electrical signal in repetitive periods.

* * * * *